Figure 1:
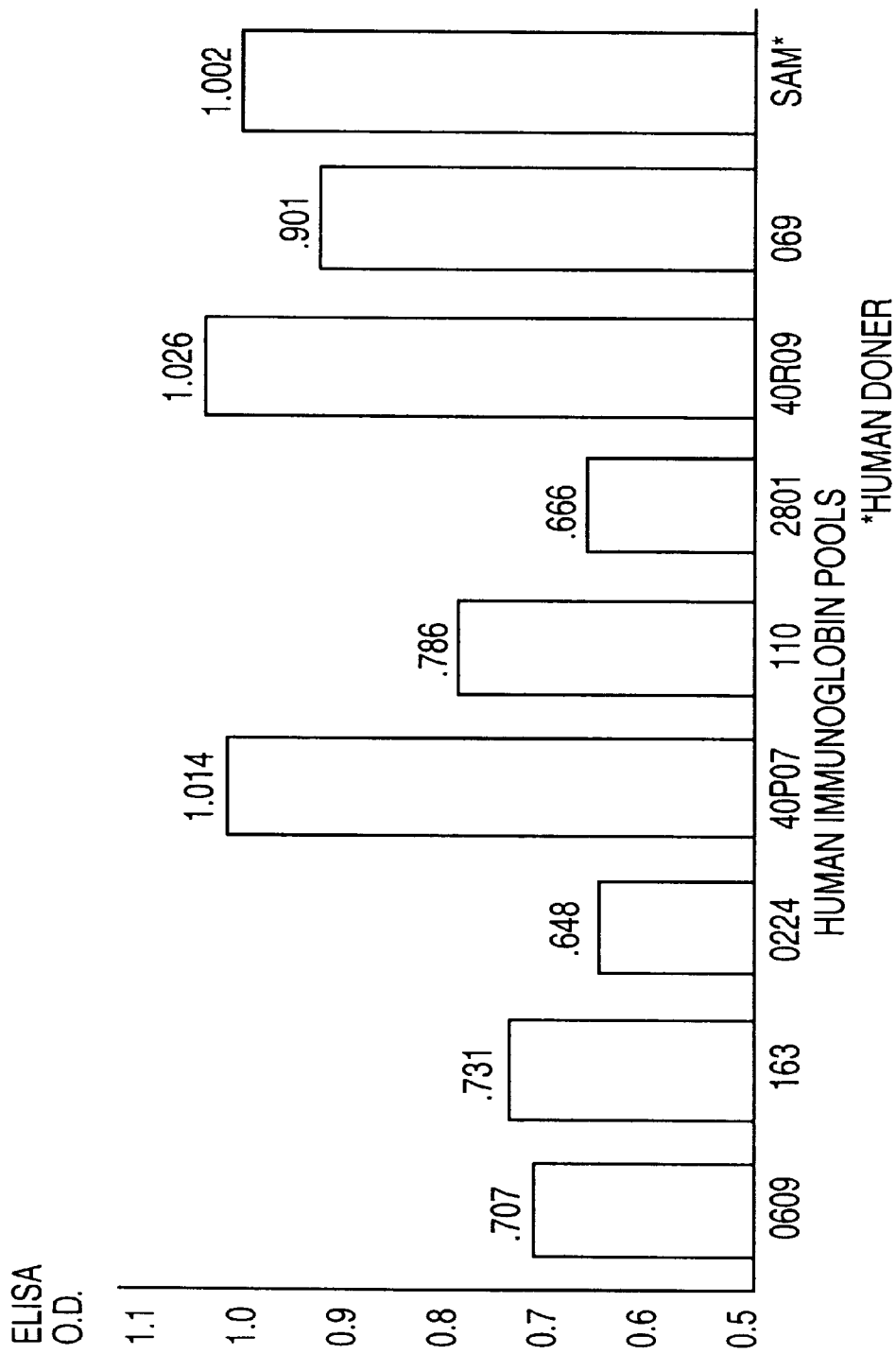

United States Patent [19]

Fischer

[11] Patent Number: 5,955,074
[45] Date of Patent: Sep. 21, 1999

[54] DIRECTED HUMAN IMMUNE GLOBULIN FOR THE PREVENTION AND TREATMENT OF STAPHYLOCOCCAL INFECTIONS

[75] Inventor: Gerald W. Fischer, Bethesda, Md.

[73] Assignee: Henry M. Jackson Foundation for the Advancement of Military Medicine, Rockville, Md.

[21] Appl. No.: 08/459,164

[22] Filed: Jun. 2, 1995

Related U.S. Application Data

[63] Continuation of application No. 08/296,133, Aug. 26, 1994, abandoned, which is a continuation of application No. 08/804,317, Feb. 25, 1992, abandoned, which is a continuation of application No. 07/601,089, Oct. 22, 1990, abandoned.

[51] Int. Cl.$^6$ .................................................. A61K 39/395
[52] U.S. Cl. .................... 424/130.1; 424/85.8; 435/7.33; 435/252.8
[58] Field of Search .................................. 435/7.33, 68.1, 435/252.8, 822; 514/54; 424/130.1, 85.8

[56] References Cited

U.S. PATENT DOCUMENTS

| 4,027,010 | 5/1977 | Kiselev et al. | 424/87 |
| 4,197,290 | 4/1980 | Yoshida | 424/165.1 |
| 4,482,483 | 11/1984 | Curry et al. | . |
| 5,530,102 | 6/1996 | Gristina et al. | 530/391.1 |

FOREIGN PATENT DOCUMENTS

| WO 93/09811 | 5/1993 | WIPO . |
| WO 93/19373 | 9/1993 | WIPO . |

OTHER PUBLICATIONS

Wedren, H., Scand. J. Urol. Nephrol. Suppl., 1989, vol. 123, p1–36.
Fischer, GW. Pediatric Clinic of North America, vol. 35(3), Jun. 1988, p517–533.
Kamdar, SS et al, Indian J. Med. Res., Oct. 1990, vol. 92, p337–40.
Yang, KD et al, J. of Infect. Dis. vol. 159(4) Apr. 1989, p701–707.
Gunn, BA., J. of Clinical Microbiol., Mar. 1989, vol. 27(3), p507–511.
Verhoff, J. et al, Scan. J. Infect. Dis, Suppl. vol. 41, p56–63, 1983.
Clark, LA et al, J. Clin. Path., 1986, vol. 39, p856–860.
Conway, SP et al, Vox Sang, 1990, vol. 59(1), p6–11.
Etzoni, A et al, Acta Paediatr Scand, vol. 79, p156–161, 1990.
Gonzalez, LA et al, Pediatr. Infect. Dis. J., 1989, vol. 8(5), p315–322.
van Bronswijk et al, Immunology, 1989, vol. 67, p81–86.
Bussel, JB et al, May–Jun. 1990, 12 Suppl. 4, p5457–461, Rev. Infect. Dis.
Counter, F.T. et al, J. of Antibiotics, Jun. 1990, p616–618, vol. XLIII (6).
Clapp, D.W et al, Dec. 8, 1989, J. Pediatrics, vol. 115, p973–978.
Verhoff, J et al, Immunol. 1977, p191–197, vol. 33.
Baker, Carol J., Pediatric Res., vol. 25(4), part 2, Apr. 1989, p. 275A, abstract #1633.
Arakawa, S. et al, Nishinihon Journal of Urology, vol. 49(4), 1987, p1007–1014, English abstract, and table on p. 1010.
Weisman, E. et al, The Am. Ped. Soc. and Soc. Ped. Res., May 7–10, 1990, Abst. 1648, p. 277A.
Hague, K.N. et al, Am. J. Dis. Children, Dec. 1988, vol. 142, p1293–1296.
Carozzi, S. et al, Trans. Am. Soc. Artif. Intern. Organ, vol. XXXIV, 1988, Jul.–Sep., vol. 34(3), p635–639.
Lamperi, S. et al, Biomat. Artif. Cells Artif. Organs, 1987, vol. 15(1), p151–159.
Timmerman et al., Characterisation and Functional Aspects of Monoclonal Antibodies Specific for Surface Proteins of Coagulase–Negative Staphylococci, J. Med. Microbiol., vol. 35, pp. 65–71 (1991).
Niizuma, T, Chem. Abs., vol. 115, p713, #181022v, 1990.
Biotechnology Newswatch, A. McGraw–Hill Production, pp. 2–3, Oct. 4, 1993.
Ichiman et al., Induction of Resistance with Heat–Killed Unencapsulated Strains of *Staphylococcus epidermidis* Against Challenge with Encapsulated Strains of *Staphylococcus epidermidis*, Microbiol. Immunol., vol. 33 (4), pp. 277–286, (1989).
Ichiman et al., "Protective Antibodies in Human Sera Against Encapsulated Strains of *Staphylococcus epidermidis*," J. Appl. Bacteriol., 63:165–169 (1987).
Clark et. al., "Opsonic Activity of Intravenous Immunoglobulin Preparations Against *Staphylococcus epidermidis*," J. Clin. Pathol., 39:856–860 (1986).
Clark et al., "Opsonic Requirements of *Staphylococcus epidermidis*," J. Med. Microbiol., 22:1–7 (1986).
Fleer et al., "Opsonic Defense to *Staphylococcus epidermidis* in the Premature Neonate," J. Infect. Dis., 152:930–937 (1985).
Fleer et al., "Septicemia due to Coagulase–negative Staphylococci in a Neonatal Intensive Care Unit: Clinical and Bacteriological Features and Contaminated Parenteral Fluids as a Source of Sepsis," Pediatr. Infect. Dis., 2:426–431 (1983).
Fischer et al., "Diminished Bacterial Defenses with Intralipid," The Lancet, 2:819–820 (1980).
Yoshida et al., "Immunological Response to a Strain of *Staphylococcus epidermidis* in the Rabbit: Production of Protective Antibody," J. Med. Microbiol., 11:371–377 (1977).
Yoshida et al., "Mouse Virulent Strain of *Staphylococcus epidermidis*," Jap. J. Microbiol., 20:209–217 (1976).

(List continued on next page.)

*Primary Examiner*—Carol A. Spiegel
*Assistant Examiner*—Ginny Allen Portner
*Attorney, Agent, or Firm*—Finnegan, Henderson, Farabow, Garrett & Dunner

[57] ABSTRACT

This invention is directed to a Directed Human Immoglobulin and compositions thereof for preventing or treating staphylococcal infections such as *S. epidermidis* in neonates.

6 Claims, 3 Drawing Sheets

OTHER PUBLICATIONS

West et al., "Detection of Anti–teichoic Acid Immunoglobulin G Antibodies in Experimental *Staphylococcus epidermidis* Endocarditis," *Infect. and Immun.*, 42:1020–1026 (1983).

Espersen et al., "Enzyme–linked Immunosorbent Assay for Detection of *Staphylococcus epidermidis* Antibody in Experimental *S. epidermidis* Endocarditis," *J. Clin. Microbiol.*, 23:339–342 (1986).

Ichiman et al., "Relation of Human Serum Antibody Against *Staphylococcus epidermidis* Cell Surface Polysaccharide Detected by Enzyme–linked Immunosorbent Assay to Passive Protection in the Mouse," *J. Appl. Bacteriol.*, 71:176–181 (1991).

Ichiman et al., "Monoclonal IgM Antibody Protection in Mice Against Infection with an Encapsulated Strain of *Staphylococcus epidermidis*," *Can. J. Microbiol.*, 37:404–407 (1991).

Fischer et al., "Directed Immune Globulin Enhances Survival in an Intralipid Induced Neonatal Model of Lethal *Staphylococcus epidermidis* Sepsis," *Pediatr. Res.*, Abstract No. 1670, p. 281A (Apr. 1991).

C.C. Patrick, "Coagulase–negative Staphylococci: Pathogens with Increasing Clinical Significance," *J. of Pediatr.*, 116:497–507 (1990).

Freeman et al., "Association of Intravenous Lipid Emulsion and Coagulase–negative Staphylococcal Bacteremia in Neonatal Intensive Care Units," *New. Engl. J. Med.*, 323:301–308 (1990).

J. O. Klein, "From Harmless Commensal to Invasive Pathogen: Coagulase–Negative Staphylococci," *New Engl. J. Med.*, 323:339–340 (1990).

T. Niizuma, "Passive Protective Activities of Specific Human Immunoglobulin Against Strain ST67P of *Staphylococcus hyicus* Extracted from Pooled Human Sera," *Chem. Abstracts*, 115:181022v, p. 713 (1990).

T. Niizuma, "Passive Protection Activities of Specific Human Immunoglobulin Against Strain ST67P of *Staphylococcus hyicus* Extracted from Pooled Human Sera," *St. Marianna Med. J.*, 18:940–946 (1990).

Certified English translation of document No. 10.

Espersen et al., "Solid Phase Radioimmunoassay IgG Antibodies to *Staphylococcus epidermis*: Use in Serious Coagulase–negative Staphylococcal Infections," *Arch. Intern. Med.*, 147:689–693 (1987).

DIRECTED HUMAN IMMUNE GLOBULIN FOR THE PREVENTION AND TREATMENT OF STAPHYLOCOCCAL INFECTIONS

This is a continuation of prior application Ser. No. 08/296,133, filed Aug. 26, 1994, now abandoned which is a continuation of application Ser. No. 08/804,317, filed Feb. 25, 1992, abandoned, which is a continuation of application Ser. No. 07/601,089, filed Oct. 22, 1990, abandoned.

I. GOVERNMENT INTEREST

The invention described herein may be manufactured, licensed and used by or for govermental purposes without the payment of any royalties to us thereon.

II. FIELD OF THE INVENTION

This invention relates to Directed Human Immune Globulin for the prevention and treatment of staphylococcal infections.

III. BACKGROUND OF THE INVENTION

Over the last two decades, staphylococci have become important causes of infection in hospitalized patients. Because of their high prevalence on the skin, staphylococci are ideally situated to cause serious infections in debilitated or immunosuppressed patients. The staphylococcal species most frequently pathogenic in humans are *Staphylococcus aureus* (SA) and *Staphylococcus epidermidis* (SE). Both groups have developed resistance to multiple antibiotics making antimicrobial therapy difficult. In recent years SE has become a major cause of nosocomial infection in patients whose treatments include the placement of foreign materials such as cerebrospinal fluid shunts, vascular catheters or joint prostheses. SE is a common cause of post operative wound infections peritonitis in patients with continuous ambulatory peritoneal dialysis. Patients with impaired immunity (malignancy, bone marrow transplant) or those receiving parenteral nutrition through central venous catheter are also at high risk for developing SE sepsis (Patrick, J. Pediat., 1990).

SE has emerged as a common cause of neonatal nosocomial sepsis in premature infants. As shown by Fleer and colleagues, (Pediatr Infect Dis, 1983) SE infections frequently occur in immature babies that have received parenteral nutrition. Premature babies have impaired immunity with deficiencies in antibodies, complement and neutrophil function. Lipid infusion is now a standard ingredient of parenteral nutrition therapy in many nurseries and may further impair immunity to bacterial infection as disclosed by Fischer and colleagues (Lancet, 1980; 2:819–20). Recent studies have associated coagulase negative staphylococcal bacteria in neonates with lipid emulsion infusion (Freeman and colleagues, N. Engl. J. Mod, 1990). Further studies by Fleer and colleagues (J Inf Dis, 1985) showed that neonates had low levels of opsonic antibody to SE despite the fact that the sera had clearly detectable levels of IgG antibodies to SE peptidoglycan (opsonic antibodies for staphylococcus have been considered to be directed to the poptidoglycan antigens). While these studies suggested that neonatal susceptibility to SE might be related to impaired oposonic activity, it is not clear if antibodies directed against SE are opsonic or would be capable of providing protection when given passively to neonates. Further, it is unknown whether the presence of intralipid, which further impairs phagocytosis and killing of bacteria by phagocytes, would inhibit the activity of antibody.

The opsonic activity of pooled human immunoglobulin for SE was studied by Clark and colleagues (J Mod Microbiol, 1986), and showed that complement and IgG were both critical for efficient opsonization of SE. They noted, however, that in some studies complement was not required and that contrary to the report of Fleer (1985), absorption of serum with peptidoglycan may remove the opsonic activity for SE. Further studies by Clark and Easmon (1986) showed that several lots of standard intravenous immune globulin (IVIG) had variable opsonic activity for SE. One third of the IVIG lots had poor opsonization with complement and only 2 of 14 were opsonic without complement. Despite the fact that the IVIG lots are made from large plasma donor pools good opsonic antibody to SE was not uniformly present. Their studios focused on potential use of immunoglobulin to boost peritoneal defenses in patients receiving continuous ambulatory peritoneal dialysis and did not examine whether IVIG could be utilized for the prevention or treatment of bacterial sepsis, or the use of antibody to prevent or treat sepsis and lethal infection in immature or immunosuppressed patients and Specifically, no in vivo studies were done to test antibody to prevent or treat SE. There is no evidence therefore that the antibody would provide beneficial therapy in a setting of immaturity or impaired immunity.

The opsonic assays, that are currently used are slow and cumbersome for screening blood, plasma or immune globulin for antibodies to SE. It would be important to have a rapid antigen binding assay to screen for SE antibody, if that assay further correlated with opsonic activity in vitro and protection in vivo.

In order to determine if IgG is capable of enhancing protection against SE, a suitable animal model that is comparable to patients with SE infections is required. This is critical since neonates have low levels of complement and impaired neutrophil and macrophage function. While opsonic activity of immune globulin may be adequate under optimal conditions in vitro, protection may not occur in patients with immature or impaired immune systems. As has been demonstrated by Clark and colleagues (J Clin Pathol, 1986), most IVIG preparations were not opsonic when complement was removed. However, since SE has low virulence, suitable animal models of SE sepsis have not been available.

Yoshida and colleagues, (J Microbiol, 1976) reported on a virulent strain of SE that infected mature mice with 90–100% of mice dying within 24–48 hours. This model is very different from that seen in patients and may represent an unusual type of SE infection. When they analyzed 80 fresh isolates of SE from humans, they were not able to kill mice. Non-human antibody to a now SE surface polysaccharide protected the mice from the virulent SE strain. A later report by Yoshlida and colleagues (J Med Microbiol, 1977) confirmed their previous observations. Passive prophylaxis with immunization induced non-human antibody showed that the IgG fraction did not protect while the IgM fraction did provide protection. Thus demonstrating in this model that IgG antibody was not protective. As noted previously herein neonates had good levels of IgG to SE, but had low levels of opsonic antibody (Fleer and colleagues, J. Infect. Dis, 1985), consistent with the findings in this study and showing that the role of IgG in protection against SE is unclear. In 1987 the report by Ichiman and colleagues (J Appl Bacteriol, 1987) extended their animal studies to include analysis of protective antibodies in human serum against their selected virulent strains of SE. Protective antibody was found in the IgA, IgM and IgG immunoglobulin fractions. These studies are in conflict with their previous data showing that IgG was not protective and fails to establish a definitive role for any of the immunoglobulin classes (IgG, IgM or IgA).

In the animal model described by Yoshida, Ichiman and colleague mature, non-immunosuppressed mice were used and death was considered to be related to toxins not sepsis (Yoshida and colleagues, J. Microbiol, 1976). Most clinical isolates did not cause lethal infections in their model. Since quantitative blood cultures were not done, it is not known whether antibody would prevent or treat SE sepsis in immature immunosupressed patients or specifically in the presence of intralipid.

Antibody provides protection in humans against certain encapsulated bacteria such as *Hemophilus influenzae* and *Streptococcus pneumoniae*. Individuals such as young infants who are deficient in antibody are susceptible to infections with these bacteria and bacteremia and sepsis are common. When antibody to these bacteria is present it provides protection by promoting clearance of the bacteria from the blood. Immunoglobulin with antibody to *H. influenzae* and *S. pneumoniae* protects infants from sepsis with these bacteria. The article by Espersen and colleagues, (Arch Intern Mod, 1987) discloses the use of an antigen binding RIA assay to analyze IgG antibody to SE in patients with uncomplicated bacteremia and those with bacteremia and endocarditis. This assay used an ultrasonic extract of SE to identify SE specific Iga (the surface antigen in this study differs from the antigen used by Yoshida and colleagues which was obtained by a different method; gentle sonic oscillation). None of the patients with uncomplicated bactermia had IgG antibodies to SE. These data would suggest that IgG is unnecessary for effective eradication of SE from the blood. In addition, 89% of bacteremic patients with endocarditis developed high levels of IgG to SE. In these patients, IgG was not protective since high levels of IgG antibody (which may have developed late) were associated with serious bacteremia add endocarditis. Based on these studies the protective role of IgG in SE sepsis and indocarditis is not established, especially in the presence of immaturity, debilitation, intralipid infusion, or immunosuppresion. In addition, the extensive review of Patrick et al. (J. Pediat., 1990) does not include immunoglobulin as a potential prophylactic or therapeutic agent for SE infections.

It has been recognized by the medical community that SE is an important pathogen in certain high risk individuals, such as patients with foreign body implants, premature neonates and immunosuppressed patients. Accordingly there is a need for a human immune globulin that would prevent or treat SE infections such as, sepsis or endocarditis and promote clearance of SE from the blood of such high risk people.

IV. SUMMARY OF THE INVENTION

It is therefore an object of the present invention to provide a novel Directed Human Immune Globulin for preventing or treating staphylococcal infections. We have found that it is useful to screen serum (plasma) or pooled immunoglobulin for specific antibody to *S. epidermidis* to produce Directed Human Immune Globulin to this pathogen. This Directed Human Immune Globulin is different from standard human imumune globulin preparations in that it has high levels of human anti-staphylococcal antibodies that react with surface antigens of *S. epidermidis* and enhance phagocytosis and killing of *S. epidermidis* in vitro, (opsonophagocytic bactericidal activity greater than 80%). In addition, Directed Human Immune Globulin for *S. epidermidis* enhances immunity in vivo and prevents lethal infection as well as enhancing clearance of *S. epidermidis* from the blood in conditions of immaturity and impaired immunity. This is surprising since immunosuppression or immaturity would be expected to render the antibody ineffective by impairing the ability of phagocytic cells to engulf and kill the *S. epidormidis*.

It is also another advantageous object of the present invention that while standard immunoglobulin pools or normal donors do not have reliable levels of opsonic antibody for *S. epidermidis*, Directed Human Immune Globulin when given intravenously immediately provides specific antibodies to promote phagocytosis and killing of *S. epidermidis* by phagocytes. A further advantages of the present invention is that by providing opsonic antibody to immature or immunosuppressed patients infected with SE, antibiotic therapy may be enhanced by improved *S. epidermidis* clearance from the blood or site of infection. Another advantage in that since Directed Human Immune Globulin given intravenously or intramuscularly can raise the level of antibodies in the blood of patients, Directed Human Immune Globolin could prevent *S. epidermidis* from causing bacteremia and local infections.

The method of producing the Directed Human Immune Globulin for *S. epidermidis* involves:

a) screening plasma (pools of immunoglobulln or plasma; immunoglobulin or immunoglobulin preparations) for antibodies to *S. epidermidis* using an in vitro antigen-binding assay: (ELISA); followed by confirmation of functional activity using an in vitro opsonophagocytic bactericidal assay (bactericidal activity greater than 80%).

b) Protective efficacy can be documented in vivo by analyzing protective activity of the Directed Human Immune Globulin using a suckling rat model of neonatal *S. epidermidis* sepsis (mortality and bacterial clearance). We believe that this is the first in vivo model to test antibody effectiveness in the presence of immaturity and/or intralipid induced immune suppression.

These methods could be repeated using other staphylococci such as SA instead of SE to produce Directed Human Immune Globulin for *S. aureus*.

This novel Directed Human Immune Globulin for SE could be used to prevent lethal SE infections in high risk patients such as neonates and adults in intensive care units or patients with in-dwelling foreign bodies such as venous and arterial catheters or ventricular shunts. Directed Human Immune Globulin could also be used in addition to antibiotics as adjunctive therapy to enhance bacterial clearance in patients treated for SE infections.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

The terms Standard Human Immunoglobulin and Directed Human Immune Globulin for *S. epidermidis* as used in this application are defined as follows: Standard Human Immunoglobulin—human globulin that was prepared by pooling immunoglobulin from many donors, without selecting donors or screening the immunoglobulin to ensure antibody acitivity for *S. Epidermidis*.

Directed Human Immune Globulin for *S. epidermidis*—Immune globulin prepared by screening for antibody to *S. epidermidis* (Bactericidal Activity >80%), thereby providing a human immune globulin with protective levels of antibody to *S. epidermidis* and suitable for preventing or treating *S. epidermidis* infections. Bactericidal Activity—The percentage of bacteria killed with the addition of antibody, using a neutrophil mediated opsonophagocytic bactericidal assay after 2 hours of incubation at 37° C.

V. BRIEF DESCRIPTION OF THE DRAWINGS

FIG. 1

FIG. 1 shows that when several pools of human standard intravenous immunglobulin were analyzed, there was a marked difference in the antibody activity to *S. epidermidis* as measured by an antigen binding assay (ELISA, highest O.O. reading at 1½ hrs using 1:100 Dil). These were large pools of IgG, purified by several companies using various techniques. Of three pools with the highest titers, two were from Cutter Laboratories, Berkeley Calif., (40P07, 40R09) and one was from Sandoz, East Hanover, N.J. (069). One preparation from Cutter also had next to the lowest activity (2801). These data show that standard unscreened human immunoglobulin has variable levels of antibody to *S. epidermidis* and that no single method used to prepare the immunoglobulin or utilizing a large donor pool size will ensure good antibody activity to *S. epidermidis*. In addition, a donor was shown to have high antibody activity (Sam) to *S. epidermidis* demonstrating the feasibility of identifying units of plasma or, plasma donors with high levels of antibodies to staphylococcus.

FIG. 2

Figure 2:
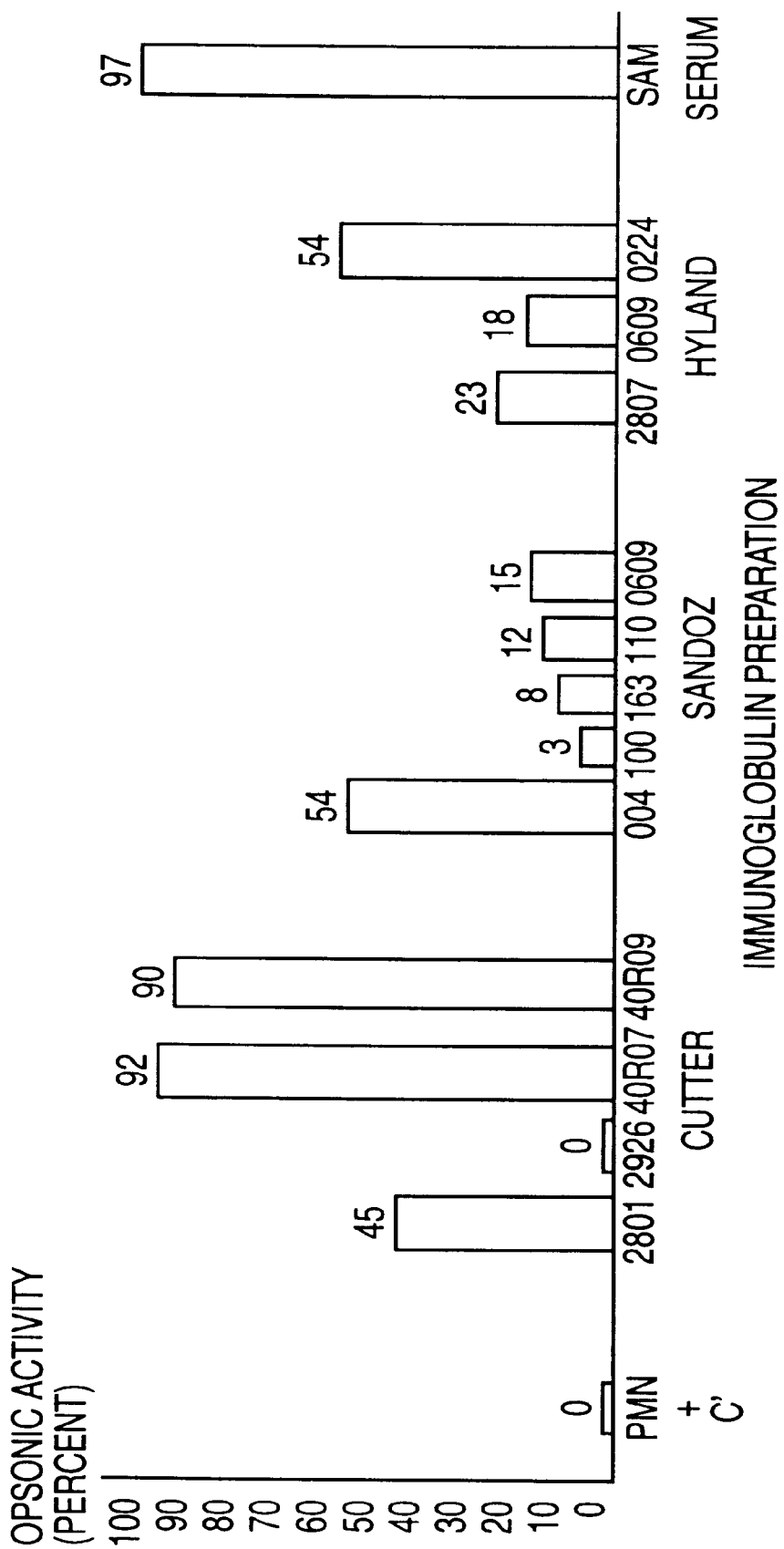

FIG. 2 shows that using an in vitro functional (opsonic) assay that measures the ability of immunoglobulin to promote phagocytosis and killing of *S. epidermidis* by neutrophils in the presence of complement, that opsonic activity is also variable in various lots and preparations of standard human immunoglobulin. The figure also shows that the immunoglobulins identified by ELISA as having high levels of antibody to *S. epidermidis* also had high levels of functional antibody in vitro. This is critical since this study shows that IgG that binds to TCA extracted *S. epidermidis* antigen will promote phagocytosis and killing of *S. epidermidis*. Therefore, using in vitro screening assays, one could select a Directed Human Immune Globulin for *S. epidermidis* that would have reliable levels of antibody to prevent or treat *S. epidermidis* infections. It also shows that unscreened immune globulin would not provide reliable protection, since many standard human immunoglobulin lots have little or no opsonic activity for *S. epidermidis*. Hance, standard human immune globulin would not ensure uniformly high levels of antibody to SE and would not be uniformly protective despite the fact that large numbers of donors might be expected to provide good levels of antibody to a common bacteria such as *S. epidermidis*.

FIG. 3

Figure 3:
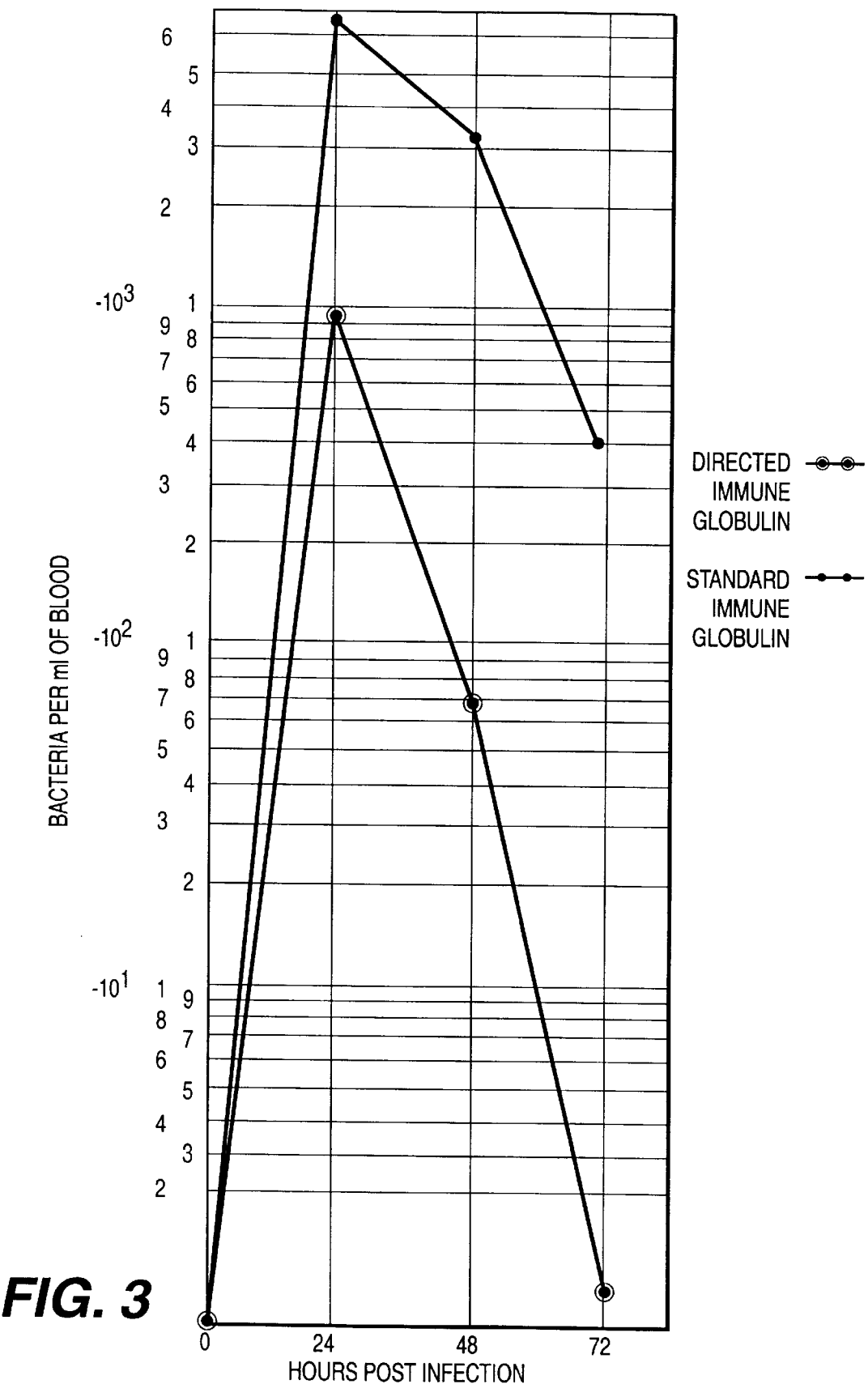

FIG. 3 shows that Directed Immune Globulin protects animals from developing prolonged *S. epidermidis* bacteremia while standard immune globulin did not. Animals treated with Directed Immune Globulin had lower peak bacteremia levels ($9.2 \times 10^2$ vs. $6.5 \times 10^3$) and cleared the bacteremia more efficiently (at 72 hours, 5 bact. per ml vs. 380 bact. per ml; geometric mean level). In addition 72 hours after infection, 18/24 (75%) animals given Directed Immune Globulin had cleared their bacteremia and 100% survived, while only 4/20 (20%) animals given standard immune globulin died and only 1/16 (6%) cleared their bacteremia during that 72 hour period. In addition to prevention, since Directed Immune Globulin enhanced *S. epidermidis* clearance, it would be a valuable adjunct to antibiotic therapy for people infected with *S. epidermidis*, since many of these patients have imparied immunity and may not clear the bacteria efficiently.

VI. DETAILED DESCRIPTION OF PROFFERED EMBODIMENTS

EXAMPLES

The herein offered examples provide methods for illustrating, without any implied limitation, the practice of this invention in the production of Directed Human immune Globulin for *Staphylococcus epidermidis* and the use of said Immune Globulin for the prevention or treatment of infections caused by *Staphylococcus epidermidis*.

The profile of the representative experiments have been chosen to illustrate methods for producing Directed Human Immune Globulin to *S. epidermidis* and to demonstrate its usefulness to prevent or treat *S. epidermidis* infections.

Materials and Methods

Staphylococcal Strains: Although any *S. epidermidis* strains could be used, in these experiments we used two strains from the American Type Culture Collection, Rockville, MD (ATCC #31432 and ATCC #35984). A clinical isolate (Hay) from the blood of a child with *S. epidermidis* sepsis was also used and is also on deposit at the American Type Culture Collection.

Materials and Methods

Immunoglobulin: Standard Intravenous Immunoglobulin was used in these experiments to represent large immunoglobulin pools. Preparations from several companies wore analyzed for comparison, to include Gamimmune, Cutter Laboratories Inc. Berkeley, Calif.; Sandoglobulin, Sandoz, East Hanover, N.J.; Gammagard, Hyland, Los Angeles, Calif. Serum from individual donors were also analyzed for antibody activity to *S. epidermidis*.

Trichloroacetic Acid (TCA) Antigen Extraction

*Staphylococcus epidermidis* strains (ATCC #35984, ATCC #31432 and Hay) were grown to log phase at 37° C. in 1000 ml of Tryptic Soy Broth (Difco). The bacteria were then centrifuged at 2500 RPM for 10 minutes and the supernatant was aspirated and discarded. The bacterial button was resuspended in 200 ml of 2% trichloroacetic acid (TCA) and stirred overnight at 4° C. The mixture was then centrifuged at 2500 RPM for 10 minutes and the supernatant aspirated. To the supernatant, 4 volumes of absolute ethanol were added and refrigerated overnight at 4° C. After centrifugation at 2500 RPM for 10 minutes, the supernatant was removed and discarded. Then, five milliliters of normal saline was added to the antigen precipitate, it was cultured to ensure sterility and then lyophilized for storage.

Antigen Binding Studies Using Enzyme-Linked Immunoabsorbent Assay (ELISA)

*S. epidermidis* Antigen was dissolved in carbonate buffer at a concentration of 25 micrograms/ml. To each well of A 96-well flat-bottomed microtiter plate (NUNC, Roskilide, Denmark) 100 microliters were added and stored at 4° C. until used. Immunoglobulin was diluted to 1% and 2-fold dilutions prepared in phosphate-buffered saline-Tween. To each well was added 100 microliters of the serial dilutions and the plates were incubated for 1 hour at 4° C. The plates were washed four times with $H_2O$-Tween. Alkaline phosphatase linked goat anti-Human IgG (100 microliters; 1:250) was added, the plates were incubated for 1 hour at 4° C. and then washed H$_2$O-Tween and 100 microliters of P-nitrophenyl phosphate substrate in diethanolamine buffer were added. After 90 minutes of incubation at room temperature, the color development was determined by absorbance at 405 nm.

Opsonic Assay:

To determine the functional antibody to *S. epidermidis* in the immune globulin pools and sera, a neutrophil mediated bactericidal assay was used. Neutrophils were isolated from adult venous blood by dextran sedimentation and ficall-hypaque density centrifugation. Utilizing a microtiter plate assay that requires a total volume of 0.1 ml/well, washed noutrophils (approximately 10$^6$ cells) were added to round-bottomed microtliter wells along with 3×10$^4$ approximately mid-log phase bacteria. Newborn rabbit serum (10 microliters; screened to assure absence of antibody to *S. epidermidis*) was used as a source of active complement. Forty microliters of 5% standard immune globulin (or serum) was added and the microtiter plates were incubated at 37° C. with constant, vigorous shaking. Samples (10 microliters) were taken from each well at zero time and after 2 hours of incubation, diluted, vigorously vortexed to disperse the bacteria and cultured on blood agar plates overnight at 37° C. to quantitate the number of viable bacteria. Controls consisted of neutrophils alone, complement alone and neutrophils plus complement.

Staphylococcal Sepsis Model:

A suckling rat model was used to determine the in vivo activity of antibody to *S. epidermidis*. Wistar rats (2 days old) were given 0.2 ml of 20% Intralipid (Cutter, Berkeley Calif.,) intraperitoneally at 0800 and 1400. At three days of age each animal was again given, 0.2 ml of 20% intralipid at 0800 and 1400 and 0.2 ml of 5% immunoglobulin or serum was given IP. Shortly after the last dose of intralipid, 0.05 ml (approx. 5×10$^7$) mid log phase *S. epidermidis* wore injected subcutaneously just cephalad to the tail. Suckling rats less than 24 hours old also develop lethal *S. epidermidis* sepsis when infected with 10$^7$–10$^8$ *S. epidermidis* subcutaneously. To analyze bacteremia levels in selected animals, 0.01 ml of blood was obtained from the tails of the suckling rats, 24, 48, and 72 hours after infection. The blood was collected under sterile conditions in micropipettes and serially diluted in Tryptic Say Broth (Difco). Bacteria were subcultured onto plates to ensure *S. epidermidis* bacteremia and all animals were followed five days to determine survival.

Results

Antigen Binding Activity of Human Immunoglobulin for *S. epidermidis*.

The results of the ELISA testing of several standard immunoglobulin preparations for antibody to *S. epidermidis* are presented in FIG. 1. Most standard immune globulins contained low levels of antibody to *S. epidermidis*. However, by screening for antibody to TCA extracted antigens of *S. epidermidis*, some immunoglobulin lots and serum from one volunteer donor were found to have increased levels of antibody to *S. epidermidis* (O.D. readings 1.014, 1.026, and 1.002). variations in antibody to *S. epidermidis* occurred between preparations prepared by different techniques and lot to lot variation in a single preparation was seen as well, indicating that all immunoglobulin pools were not the same.

Opsonic Activity of Human Immunoglobulins for *S. epidermidis*.

All antibody directed against a given organism may not enhance immunity and provide enhanced protection from infection. Stated differently, antibodies can bind to bacteria and yet not enhance opsonization in vitro or clearance from the blood of an infected host. Therefore a functional assay was also utilized to determine if the antibody to *S. epidermidis* detected by ELISA was also capable of promoting phagocytosis and killing of the organism by neutrophils (FIG. 2). opsonic antibody activity ranged from low (<25% bactericidal activity), to moderate activity (25–80%) and a few had high bactericidal activity (>80%). Therefore two standard human immune globulin preparations with high bactericidal activity were selected as Directed Human Immune Globulin for *S. epidermidis* based on in vitro assays that measured antibody binding to TCA *S. epidermidis* antigens and opsonic antibody activity determined by in vitro testing. Serum from a single donor also had good opsonic activity for *S. epidermidis* (>80% opsonophagocytic bactericidal activity). While serum and plasma from several individuals have been studied only this donor had high opsonic activity. Therefore donor screening could detect individual blood or plasma donors that could contribute immunoglobulin that could be pooled as an alternate method to produce a Directed Human Immune Globulin for *S. epidermidis*. In addition blood or plasma units could be screened for pooling as well.

Animal Protection Studies

Discription of Tables

Table 1

Table 1 shows the effect of Directed Human Immunoglobulin for *S. epidermidis* (40R09) (which was selected by ELISA and opsonic assay screening) compared to standard human lmmunoglobulin (that had moderate activity for *S. epidermidis*) and saline control. Table 1 shows that untreated control animals had about a 50% mortality while animals given Directed Immune Globulin for *S. epidermidis* were fully protected (NO mortality). Standard immune globulin gave only partial protection. Other standard immune globulin lots with lower levels of antibody to *S. epidermidis* would be even less effective, since mortality was much higher with saline. However, one would not expect that Directed Immune Globulin would be always 100% effective, but that it would consistently improve survival over standard immune globulin or untreated animals.

Table 2

Table 2 demonstrates that Directed Immune Globulin produced in rabbits by immunization (*S. epidermidis* vaccine) produced survival similar to Directed Human Immune Globulin produced by screening immunoglobulin for antibody to *S. epidermidis*. Immunization of individuals with *S. epidermidis* vaccine and collecting plasma for immunoglobulin extraction would be another method for producing Directed Human Immune Globulin for preventing or treating *S. epidermidis* infections.

Table 3

Table 3 shows that intralipid causes a dose related increased mortality in suckling rats infected with *S. epidermidis*. Control animals receiving Intralipid alone had 100% survival (43/43) while immature rats given 16 gm/kg of Intralipid had only 46% survival (6/13). The high dose of Intralipid appears to impair the immune system sufficiently to allow the normally avirulent *S. epidermidis* to overwhelm the baby animals.

Table 4

Table 4 shows that normal 3 day old suckling rats not given Intralipid, but infected with *S. epidermidis* develop bacteremia. However, over 72 hrs their immune system is able to clear the organisms from the blood and all of the baby rats survive.

Table 1 shows the Directed Human Immune Globulin for S. epidermidis (selected by screening standard immumoglobulin for opsonic or antigen binding activity for S. epidermidis) provides complete protection from lethal infection in the setting of impaired immunity with Intralipid while standard immune globulin (with moderate antibody levels) had only partial protection (1 out of 5 aminals died compared to about 50% with saline). Additional studies with another immunoglobulin preparation, (Alpha Pharmaceuticals; Directed Human Immune Globulin 8016A >90% opsonic activity, versus standard human immune globulin, 8007A <50% opsonic activity) showed that the Directed Human Immune globulin also provided enhanced survival (8016A-64/95 (67%) vs. 8007A-39/90 (43%)) over standard human immune globulin. Even more striking was the fact that the Directed Human Immune Globulin decreased the peak level of S. epidermidis bacteremia and promoted rapid clearance of the bacteria (FIG. 3). These studies showed that antibody was important for protection against S. epidermidis enhanced bacterial clearance from the blood and could be an effective prophylactic or therapeutic modality even in the immature host with impaired immunity. Many of the animals treated with standard human immune globulin remained bacteremic 72 hours after infection while only 1/20 animals was still bacteremic at 72 hours after receiving the Directed Human Immune Globulin. In addition the mean bacteremia level at 72 hours was markedly different (bacteremia with Directed Human Immune Globulin $0.5 \times 10^1$ vs. bacteramia with standard human immune globulin $3.8 \times 10^2$).

In further studies, rabbit Directed Immune Globulin for S. epidermidis was produced by immunizing rabbits with S. epidormidis vaccine. The vaccine induced Directed Immune Globulin was compared with Directed Human Immune Globulin produced by screening immunoglobulin for antibody to S. epidermidis (Table 2). vaccine induced Directed Immune Globulin had similar protective activity to Directed Human Immune Globulin produced by screening (9/11 vs. 12/13 survived) and each was better than controls (11/19 survived). These data show that S. epidermidis vaccine induced antibody could be used for prevention and treatment of S. epidermidis infections and that vaccine could be used to produce a Directed Human Immune Globulin.

TABLE 3

Many bacteria such as S. epidermidis are not pathogenic in normal people. However, in babies with an immature immune system or impaired immunity as is soon with intralipid, S. epidermidis may cause sepsis and death. It is critical therefore, that any animal model to test antibody effectiveness should include these factors. To our knowledge this is the first time that antibody to Staphylococcus epidermis has been shown to provide protection and enhance bacterial clearance in an immature and/or immunosuppressed host. Intralipid given in dosage up to 16 gm/kg did not cause death in any baby animals (controls, table 3). In the absence of Intralipid, the 3 day old animals will become bacteremic with S. epidermidis after infection, but will clear the infection over 72 hours and survive (Table 4). However, Intralipid did impair immunity in a dose related fashion and when the 3 day old animals were infected with S. epidermidis lethal sepsis occurred in up to 67% of the animals. Baby rats in the first day of life also do not clear bacteriemia well (due to immature immunity) and develop lethal sepsis. In these models baby rats were unable to clear the S. epidermidis bacteremia and developed lethal sepsis. Directed Human Immune Globulin was able to enhance survival and promote bacterial clearance while standard human immune globulin did not enhance clearance (FIG. 3).

TABLE 4

When SE is injected into normal baby rats, they become bacteremic in 2 hours and then begin to slowly clear the bacteria from the blood. All of the animals cleared the bacteremia 72 hours after the infection. thus suggesting that under normal circumstances neonatal immunity while impaired can eventually control SE. However, studies in rats infectedd with S. epidermidis shortly after birth have demonstrated that they can also develop a lethal infection.

TABLE 1

Effectiveness of Standard Immune Globulin
and Directed Immune Globulin to
Staphylococcus epidermidis in Providing Protection
from lethal S. epidermidis Infection
in a Suckling Rat Model

| Immunoglobulin Type | Treated | Died | % Mortality |
|---|---|---|---|
| Direct Immune Globulin* (40R09) | 24 | 0 | 0 |
| Standard Immune Globulin* Control | 20 | 4 | 20% |
| Untreated** | 13 | 7 | 54% |
| Uninfected** | 11 | 0 | 0 |

*#20–23 - 3/25/90
**#8 - 2/11/90, #4 - 1/29/90

TABLE 2

Comparision of Therapeutic Efficacy of
Vaccine Induced Anti-staphylococcal
Directed Immune Globulin with Screened
Directed Immune Goobulin in a S. epidermidis Sepsis Model*

| Treatment | Exp. | Treated | Survived | % Survived |
|---|---|---|---|---|
| Vaccine Induced Directed Immune Globulin | 16,19 | 11 | 9 | 82% |
| Screened Directed Immune Globulin (40R09) | 17,18 | 13 | 12 | 92% |
| Saline Control | 16,17 18,19 | 19 | 11 | 58% |

*1990 Studies

TABLE 3

Animal Model: Effect of Intralipid Dosage on
Staphylococcus epidermidis mortality on suckling rats

| Intralipid | Survival | |
|---|---|---|
| Dose | Infected | Control |
| 4 gm/kg | 10/10 (100%) | 7/7 (100%) |
| 8 gm/kg | 10/13 (75%) | 9/9 (100%) |
| 12 gm/kg | 7/12 (58%) | 11/11 (100%) |
| 16 gm/kg | 6/13 (46%) | 11/11 (100%) |
| *16 gm/kg | 2/6 (33%) | 5/5 (100%) |

Infection with S. epidermidis (Haywood); approximately $10^7$ bacteria SQ.
Standard model starts IL on day 2 of life with infection after last IL dose on day 3 if full 4 doses given.
*IL started on day 1 of life with infection after the 4th dose on day 2.

TABLE 4

*Staphylococcus epidermidis* Bacteremia Levels in Normal Suckling Rats Given Normal Saline Instead of Intralipid

| Time Post Infection | Number Bacteremic | Per Cent Bacteremic | Bacteremia Level* |
|---|---|---|---|
| 2 hours | 8/8 | 100 | $3.8 \times 10^2$ |
| 4 hours | 7/8 | 87.5 | $1.3 \times 10^2$ |
| 6 hours | 8/8 | 100 | $7.5 \times 10^2$ |
| 24 hours | 6/8 | 75 | $8.8 \times 10^1$ |
| 48 hours | 3/8 | 37.5 | $0.5 \times 10^1$ |
| 72 hours | 0/8 | 0 | 0 |

Exp. 93 + 94: 8/8 survived
*Mean number of bacterial per ml of blood

We claim:

1. A method of preventing and treating *Staphylococcus epidermidis* infections in neonates, comprising:
   administering to said neonates a Directed Human Immune Globulin obtained by the steps:
   a) obtaining a source of immune globulin from the group consisting of serum, plasma, and an immunoglobulin pool;
   b) in a binding screen, screening the immune globulin source for specific binding for *Staphylococcus epidermidis* and selecting the source which evidences specific binding; and
   c) in an activity screen, screening the immune globulin source of step b) for 80% opsonophagocytic bactericidal activity against *Staphylococcus epidermidis* and selecting a source having at least 80% opsonophagocytic bactericidal activity against *Saphylococcus epidermidis*.

2. The method of claim 1 in which the binding screen is an enzyme-linked immunosorbent assay.

3. The method of claim 2 in which the activity screen is an in vitro complement-dependent neutrophil opsonization assay.

4. A method of preventing and treating *Stahylococcus epidermidis* infections in neonates, comprising:
   administering to mid neonates a Directed Human Immune Globulin obtainable by the steps:
   a) obtaining a source of immune globulin from the group consisting of serum, plasma, and an immunoglobulin pool;
   b) in a biding screen, screening the immune globulin source for specific big for *Staphylococcus epidermidis* and selecting the source which evidences specific binding; and
   c) in an activity screen, screening the immune globulin source of step b) for 80% opsonophagocytic bactericidal activity against *Staphylococcus epidermidis* and selecting a source having at least 80% opsonophagocytic bactericidal activity against *Staphylococcus epidermidis*.

5. The method of claim 4 in which the binding screen is an enzyme-linked immunosorbent assay.

6. The method of claim 4 in which the activity screen is an in vitro complement-dependent neutrophil opsonization assay.

* * * * *

UNITED STATES PATENT AND TRADEMARK OFFICE
CERTIFICATE OF CORRECTION

PATENT NO. : 5,955,074

DATED : September 21, 1999

INVENTOR(S) : Gerald W. Fischer

It is certified that error appears in the above-identified patent and that said Letters Patent is hereby corrected as shown below:

IN THE CLAIMS:

Claim 4, col. 12, line 17, "big" should read --binding--.

Signed and Sealed this

Twenty-first Day of December, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,955,074

DATED : September 21, 1999

INVENTOR(S) : Gerald W. Fischer

It is certified that errors appear in the above-identified patent and that said Letters Patent is hereby corrected as shown below:

Col. 11, line 15, last line of "Table 4", correct the spelling of "bacteria."

Claim 1, column 12, line 2, change "Saphylococus" to --*Staphylococcus*--.

Claim 4, column 12, line 9, change "Saphylococus" to --*Staphylococcus*--.
column 12, line 11, change "mid" to --said--; and
column 12, line 16, change "biding" to --binding--.

Signed and Sealed this

Ninth Day of May, 2000

Q. TODD DICKINSON

*Attest:*

*Attesting Officer*          *Director of Patents and Trademarks*

UNITED STATES PATENT AND TRADEMARK OFFICE
CERTIFICATE OF CORRECTION

PATENT NO.    : 5,955,074
DATED         : September 21, 1999
INVENTOR(S)   : Gerald W. Fischer It is certified that error appears in the above-identified patent and that said Letters Patent is hereby corrected as shown below:

IN THE CLAIMS

Column 12, claim 3, line 1, change "of claim 2" to --of claim 1--.

Signed and Sealed this

Twenty-third Day of May, 2000

Attest:

Q. TODD DICKINSON

*Attesting Officer*  *Director of Patents and Trademarks*